(12) United States Patent
Dahlquist et al.

(10) Patent No.: US 10,011,809 B2
(45) Date of Patent: Jul. 3, 2018

(54) LOW ALKALINE LOW TEMPERATURE WARE WASH DETERGENT FOR PROTEIN REMOVAL AND REDUCING SCALE BUILD-UP

(71) Applicant: Ecolab USA Inc., Saint Paul, MN (US)

(72) Inventors: Erin Jane Dahlquist, West St. Paul, MN (US); Steven E. Lentsch, St. Paul, MN (US); Terrence P. Everson, Eagan, MN (US); Carter M. Silvernail, Burnsville, MN (US)

(73) Assignee: Ecolab USA Inc., Saint Paul, MN (US)

( * ) Notice: Subject to any disclaimer, the term of this patent is extended or adjusted under 35 U.S.C. 154(b) by 0 days.

(21) Appl. No.: 15/433,157

(22) Filed: Feb. 15, 2017

(65) Prior Publication Data

US 2017/0158991 A1   Jun. 8, 2017

Related U.S. Application Data (60) Division of application No. 14/242,521, filed on Apr. 1, 2014, now Pat. No. 9,605,236, which is a
(Continued)

(51) Int. Cl.
*C11D 3/395* (2006.01)
*C11D 11/00* (2006.01)
(Continued)

(52) U.S. Cl.
CPC .......... *C11D 11/0023* (2013.01); *A01N 59/08* (2013.01); *B08B 3/08* (2013.01);
(Continued)

(58) Field of Classification Search
CPC .............. C11D 7/14; C11D 7/16; C11D 7/265
(Continued)

(56) References Cited

U.S. PATENT DOCUMENTS 5,158,710 A   10/1992  VanEenam
6,812,195 B2  11/2004  Wierenga et al.
(Continued)

FOREIGN PATENT DOCUMENTS

EP   03812808   12/1997
EP   2166092    3/2010
(Continued)

OTHER PUBLICATIONS

Ecolab USA, Inc, "Extended European Search Report", issued in connection to European Application No. 13848917.4, dated May 18, 2016, 10 pages.
(Continued)

*Primary Examiner* — Gregory Webb
(74) *Attorney, Agent, or Firm* — McKee, Voorhees & Sease, PLC (57) ABSTRACT

Caustic-free detergent compositions are provided. Detergent compositions including an aminocarboxylate, water conditioning agent, non-caustic source of alkalinity and water beneficially do not require the use of additional surfactants and/or polymers to provide suitable detergency and prevent scale build-up on treated surfaces and enhance protein removal from the treated surfaces. Beneficially the detergent compositions have a concentrate pH less than about 11.5. The detergent compositions are used with a sanitizer to employ the low alkaline detergent compositions are particularly suitable for use as low temperature ware wash detergents that beneficially reduce scale build-up. Methods of employing the low alkaline detergent compositions are also provided.

19 Claims, 1 Drawing Sheet

Related U.S. Application Data continuation-in-part of application No. 13/661,154, filed on Oct. 26, 2012, now Pat. No. 9,574,163.

(51) Int. Cl.

| | | |
|---|---|---|
| *C11D 7/14* | (2006.01) | |
| *C11D 7/16* | (2006.01) | |
| *C11D 7/26* | (2006.01) | |
| *C11D 7/36* | (2006.01) | |
| *A01N 59/08* | (2006.01) | |
| *B08B 3/08* | (2006.01) | |

(52) U.S. Cl.
CPC .................. *C11D 7/14* (2013.01); *C11D 7/16* (2013.01); *C11D 7/265* (2013.01); *C11D 7/36* (2013.01); *B08B 2203/007* (2013.01)

(58) Field of Classification Search
USPC ........................................................ 510/220
See application file for complete search history.

(56) References Cited

U.S. PATENT DOCUMENTS

| | | | |
|---|---|---|---|
| 6,835,702 | B2 | 12/2004 | Herdt et al. |
| 6,835,706 | B2 | 12/2004 | Lentsch et al. |
| 7,642,224 | B2 | 1/2010 | McRae et al. |
| 7,902,137 | B2 | 3/2011 | Kneipp et al. |
| 8,123,867 | B2 | 2/2012 | Tropsch |
| 2008/0015133 | A1 | 1/2008 | Rigley et al. |
| 2008/0274930 | A1 | 11/2008 | Smith et al. |
| 2010/0000579 | A1 | 1/2010 | Reinbold et al. |
| 2010/0160202 | A1 | 6/2010 | Housmekerides et al. |
| 2010/0317559 | A1 | 12/2010 | Ryther et al. |
| 2011/0021403 | A1 | 1/2011 | Miralles et al. |
| 2011/0053819 | A1 | 3/2011 | Preuschen et al. |
| 2011/0071065 | A1 | 3/2011 | Silvernail et al. |
| 2011/0257431 | A1 | 10/2011 | Baumann et al. |
| 2011/0301072 | A1 | 12/2011 | Smith et al. |
| 2012/0010117 | A1 | 1/2012 | Seebeck et al. |
| 2012/0053104 | A1 | 3/2012 | Olson et al. |
| 2012/0067373 | A1 | 3/2012 | Souter et al. |
| 2012/0108484 | A1 | 5/2012 | Becker et al. |
| 2012/0165237 | A1 | 6/2012 | Silvernail |
| 2013/0045909 | A1 | 2/2013 | Silvernail et al. |
| 2013/0068254 | A1 | 3/2013 | Besse et al. |
| 2013/0252871 | A1 | 9/2013 | Olson et al. |
| 2014/0031273 | A1 | 1/2014 | Walters et al. |

FOREIGN PATENT DOCUMENTS

| | | |
|---|---|---|
| EP | 2361964 | 8/2011 |
| WO | 0058430 | 10/2000 |
| WO | 2008095562 | 8/2008 |
| WO | 2009092699 | 7/2009 |
| WO | 2010045686 | 4/2010 |
| WO | 2011000344 A3 | 1/2011 |
| WO | 2011025624 | 3/2011 |
| WO | 2011080540 | 7/2011 |
| WO | 2011100344 | 8/2011 |
| WO | 2011116775 | 9/2011 |
| WO | 2011144699 | 11/2011 |
| WO | 2012025740 | 3/2012 |
| WO | 2012028203 A1 | 3/2012 |
| WO | 2012038755 | 3/2012 |

OTHER PUBLICATIONS

Applicant: Dahlquist, Erin Jane, et al., U.S. Appl. No. 13/661,145, filed Oct. 26, 2012.
BASF Safety Data Sheet—Trilon* M Liquid (30043459/MDS_GEN_US-EN), Version 1.0 (7 pages) Mar. 27, 2006.
Lanxess Energizing Chemistry Safety Data Sheet, 000969/09, Revised Apr. 26, 2004 (4 pages) Oct. 6, 2004.
Industrial Chemicals Division—PQ Corporation, "Bulletin 17-2A Typical Property Data for PQ Liquid Sodium Silicates", (1 page) Dec. 31, 2007.
Rohm and Haas—Material Safety Data Sheet—ACUMER (TM) 1000 Polymer (6 pages) Sep. 24, 2007.
PQ Corporation—Material Safety Data Sheet—RU Sodium Silicate Solution (5 pages) Jun. 13, 2006.
Rohm and Haas—ACUMER 1000 Scale inhibitor (2 pages) Jan. 31, 2002.
Ecolab USA Inc., PCT/US2013/064748 filed Oct. 13, 2013, "The International Search Report and the Written Opinion of the International Searching Authority, or the Declaration", dated Jan. 28, 2014.

|   |   |   |   |   | G |
|---|---|---|---|---|---|
|   |   |   |   | G |   |
|   |   |   | G |   |   |
|   |   | G |   |   |   |
|   | G |   |   | P |   |
| G |   |   |   |   |   |

US 10,011,809 B2

LOW ALKALINE LOW TEMPERATURE WARE WASH DETERGENT FOR PROTEIN REMOVAL AND REDUCING SCALE BUILD-UP

CROSS-REFERENCE TO RELATED APPLICATIONS

This application is a Divisional of U.S. application Ser. No. 14/242,521, filed Apr. 1, 2014 which is a continuation-in-part of U.S. application Ser. No. 13/661,154 entitled "Caustic Free Low Temperature Ware Wash Detergent for Reducing Scale Build-Up." filed Oct. 26, 2012, U.S. Pat. No. 9,574,163, issued Feb. 21, 2017. The entire contents of this patent application are hereby expressly incorporated herein by reference including, without limitation, the specification, claims, and abstract, as well as any figures, tables, or drawings thereof.

FIELD OF THE INVENTION

The present invention relates generally to the field of ware wash detergents and methods of employing the same. The invention more specifically relates to low alkaline detergent compositions. In particular, the low alkaline detergent compositions are low temperature ware wash detergents that beneficially reduce scale build-up and provide enhanced protein removal. Methods of employing the detergent compositions are also disclosed.

BACKGROUND OF THE INVENTION

Alkaline detergents, particularly those intended for institutional and commercial use, in combination with the presence of hard water commonly result in heavy scale formation that is difficult to control. The level of hardness in water can have a deleterious effect in many systems. For example, calcium carbonate precipitation on the surface of ware can negatively impact the aesthetic appearance of the ware, giving an unclean look. In general, hard water refers to water having a level of calcium and magnesium ions in excess of about 100 ppm expressed in units of ppm calcium carbonate. Often, the molar ratio of calcium to magnesium in hard water is about 2:1 or about 3:1. Although most locations have hard water, water hardness tends to vary from one location to another.

The control of such water hardness presents additional difficulty in ware wash applications employing high alkalinity and/or use at elevated temperatures. Traditionally, chelating agents and/or threshold agents are employed with high alkaline detergent compositions because of their ability to solubilize metal salts and/or prevent water hardness from scaling and/or precipitating. Although very high alkalinity detergent compositions provide desirable cleaning efficacy, there is a need for reducing the concentration of caustic in alkaline detergent compositions. This is a result of need for such very high alkalinity detergent compositions to be transported, handled and/or contacted by workers, each of which present safety concerns. For example, caustic detergent compositions can cause burns to exposed skin, particularly in the concentrated form. As the alkalinity of the compositions increases, the possible risk to workers also increases. Therefore, great care must be taken to protect workers who handle concentrated highly alkaline or caustic detergents.

There is also a need for continued development of low temperature dish washing machines and detergent compositions suitable for use therein. Beneficially, reducing temperatures employed in dish washing or ware wash machines results in energy savings and other benefits for consumers.

Accordingly, it is an objective of the present invention to develop detergent compositions to address at least one of these problems and/or to offer detergent compositions with usage, environmental and/or safety benefits.

Accordingly, it is an objective of the claimed invention to develop detergent compositions having low alkaline formulations. The formulations according to the invention may contain alkaline metal hydroxide or alkaline metal silicate as long as the concentrate pH is below 11.5.

A further object of the invention is a low temperature detergent compositions being caustic-free or low caustic or low alkaline and reducing and/or eliminating scale build-up of treated surfaces and/or enhanced protein removal.

A further object of the invention is to develop methods of employing caustic-free detergent compositions under low temperature ware washing conditions that further eliminate scale build-up and/or enhance protein removal on treated surfaces.

BRIEF SUMMARY OF THE INVENTION

An advantage of the invention is the use of low alkaline detergent compositions at low temperatures, such as from about 120° F. to about 140° F., without significant scale build-up on treated surfaces and/or enhanced protein removal form the treated surfaces. It is an advantage of the present invention that the low alkaline or caustic-free detergent compositions provide beneficial scale removal and/or prevention at low temperatures.

In an embodiment, the present invention provides a low alkaline detergent composition including from about 0.1-15 wt-% of an aminocarboxylate, from about 0.1-15 wt-% of a water conditioning polymer, from about 0.1-15 wt-% of a builder, from about 10-60 wt-% of an alkalinity source, and from about 20-80 wt-% of water. In an aspect of the invention, the composition is low alkaline, has a concentrate pH below about 11.5 and/or does not contain surfactants. In a further aspect of the invention, the composition reduces or eliminates scale build-up on treated surfaces and provides enhanced protein removal from the treated surfaces. In a still further aspect, a use solution of the composition has a pH less than about 9.5 and a concentrate of the composition has a pH less than about 11.5.

In a further embodiment, the present invention provides a low alkaline detergent composition including from about 1-15 wt-% of methylglycinediacetic acid, from about 0.1-15 wt-% of a water conditioning polymer selected from the group consisting of a polyarcylate, a polycarboxylate, a polycarboxylic acid and combinations thereof, from about 0.1-15 wt-% of a builder, from about 10-60 wt-% of a silicate or other low alkalinity source, and from about 30-80 wt-% of water, wherein the composition is low alkaline (or in some embodiments caustic-free), does not contain surfactants, enhances protein removal from treated surfaces, and reduces or eliminates scale build-up on treated surfaces, wherein the ratio of the methylglycinediacetic acid to the water conditioning polymer to the builder is in a ratio of from about 1:1:1 to about 5:1:10, and wherein a use solution of the composition has a pH less than about 9.5 and a concentrate of the composition has a pH less than about 11.5.

In a still further embodiment, the present invention is a method of removing scale during a wash cycle. The method may include first diluting a detergent concentrate to form a detergent use solution. The method includes washing a surface with a detergent wash solution comprising a low alkaline detergent having a pH in a use solution between about 8 and about 9.5, a concentrate pH less than about 11.5, comprising from about 1 ppm to about 250 ppm aminocarboxylate, from about 1 ppm to about 250 ppm water conditioning polymer, from about 1 ppm to about 250 ppm builder, from about 10 ppm to about 1,000 ppm alkalinity source, and water, wherein the composition is low alkaline, does not contain surfactants, enhances protein removal from treated surfaces, and reduces or eliminates scale build-up on said surfaces. In a further aspect, the temperature of the detergent wash solution in the washing step is not heated above about 140° F.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION OF THE PREFERRED EMBODIMENT

The embodiments of this invention are not limited to particular ware wash detergent compositions, which can vary and are understood by skilled artisans. It is further to be understood that all terminology used herein is for the purpose of describing particular embodiments only, and is not intended to be limiting in any manner or scope. For example, as used in this specification and the appended claims, the singular forms "a," "an" and "the" can include plural referents unless the content clearly indicates otherwise. Further, all units, prefixes, and symbols may be denoted in its SI accepted form. Numeric ranges recited within the specification are inclusive of the numbers defining the range and include each integer within the defined range.

So that the present invention may be more readily understood, certain terms are first defined. Unless defined otherwise, all technical and scientific terms used herein have the same meaning as commonly understood by one of ordinary skill in the art to which embodiments of the invention pertain. Many methods and materials similar, modified, or equivalent to those described herein can be used in the practice of the embodiments of the present invention without undue experimentation, the preferred materials and methods are described herein. In describing and claiming the embodiments of the present invention, the following terminology will he used in accordance with the definitions set out below.

The term "about," as used herein, refers to variation in the numerical quantity that can occur, for example, through typical measuring and liquid handling procedures used for making concentrates or use solutions in the real world; through inadvertent error in these procedures; through differences in the manufacture, source, or purity of the ingredients used to make the compositions or carry out the methods; and the like. The term "about" also encompasses amounts that differ due to different equilibrium conditions for a composition resulting from a particular initial mixture. Whether or not modified by the term "about", the claims include equivalents to the quantities.

The term "actives" or "percent actives" or "percent by weight actives" or "actives concentration" are used interchangeably herein and refers to the concentration of those ingredients involved in cleaning expressed as a percentage minus inert ingredients such as water or salts.

An "antiredeposition agent" refers to a compound that helps keep suspended in water instead of redepositing onto the object being cleaned. Antiredeposition agents are useful in the present invention to assist in reducing redepositing of the removed soil onto the surface being cleaned.

As used herein, the phrase "cleaning" refers to performing or aiding in soil removal, bleaching, de-scaling, de-staining, microbial population reduction, rinsing, or combination thereof.

The phrase "detergent composition" refers to the detergent composition provided as a concentrate or as a use composition according to the invention. The term "concentrate" refers to a relatively concentrated form of the detergent composition that can be diluted with a diluent to form a use composition. An exemplary diluent that can be used to dilute the concentrate to form the use composition is water. In general, the use composition refers to the composition that contacts an article to provide a desired action. For example, a ware washing detergent composition that is provided as a use composition can contact ware for cleaning the ware. In addition, the concentrate or the diluted concentrate can be provided as the use composition. For example, the concentrate can be referred to as the use composition when it is applied to an article without dilution. In many situations, it is expected that the concentrate will be diluted to provide a use composition that is then applied to an article.

As used herein, the term "microbe" or "microorganism" refers to any noncellular or unicellular (including colonial) organism. Microorganisms include all prokaryotes. Microorganisms include bacteria (including cyanobacteria), spores, lichens, fungi, protozoa, virinos, viroids, viruses, phages, and some algae. As used herein, the term "microbe" is synonymous with microorganism. Differentiation of antimicrobial "-cidal" or "-static" activity, the definitions which describe the degree of efficacy, and the official laboratory protocols for measuring this efficacy are considerations for understanding the relevance of antimicrobial agents and compositions. Antimicrobial compositions can affect two kinds of microbial cell damage. The first is a lethal, irreversible action resulting in complete microbial cell destruction or incapacitation. The second type of cell damage is reversible, such that if the organism is rendered free of the agent, it can again multiply. The former is termed microbiocidal and the later, microbistatic. A sanitizer and a disinfectant are, by definition, agents which provide antimicrobial or microbiocidal activity. In contrast, a preservative is generally described as an inhibitor or microbistatic composition. For the purpose of this patent application, successful microbial reduction is achieved when the microbial populations are reduced by at least about 50%, or by significantly more than is achieved by a wash with water. Larger reductions in microbial population provide greater levels of protection.

As used herein, the term "sanitizer" refers to an agent that reduces the number of bacterial contaminants to safe levels as judged by public health requirements. In an embodiment, sanitizers for use in this invention will provide at least a 3-log reduction and more preferably a 5-log order reduction.

These reductions can be evaluated using a procedure set out in *Germicidal and Detergent Sanitizing Action of Disinfectants*, Official Methods of Analysis of the Association of Official Analytical Chemists, paragraph 960.09 and applicable sections, 15th Edition, 1990 (EPA Guideline 91-2). According to this reference a sanitizer should provide a 99.999% reduction (5-log order reduction) within 30 seconds at room temperature, 25±2° C., against several test organisms.

As used herein, the term "substantially free" refers to compositions completely lacking the component or having such a small amount of the component that the component does not affect the performance of the composition. The component may be present as an impurity or as a contaminant and shall be less than 0.5 wt-%. In another embodiment, the amount of the component is less than 0.1 wt-% and in yet another embodiment, the amount of component is less than 0.01 wt-%. For example, in an aspect of the invention, the detergent compositions are substantially caustic-free. Preferably, the detergent compositions are caustic-free. In still other aspects, the detergent compositions are low alkaline.

The term "threshold agent" refers to a compound that inhibits crystallization of water hardness ions from solution, but that need not form a specific complex with the water hardness ion. Threshold agents suitable for various cleaning applications include but are not limited to a polyacrylate, a polymethacrylate, an olefin/maleic copolymer, and the like. Further description of particularly suitable threshold agents according to the invention is disclosed herein.

As used herein, the term "ware" refers to items such as eating and cooking utensils, dishes, and other hard surfaces such as showers, sinks, toilets, bathtubs, countertops, windows, mirrors, transportation vehicles, and floors. As used herein, the term ware preferentially refers to items such as eating and cooking utensils. Ware also refers to items made of various substrates, including glass, metal, plastic, etc. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET). As used herein, the term "ware washing" refers to washing, cleaning, or rinsing ware.

The term "weight percent," "wt-%," "percent by weight," "% by weight," and variations thereof, as used herein, refer to the concentration of a substance as the weight of that substance divided by the total weight of the composition and multiplied by 100. It is understood that, as used here, "percent," "%," and the like are intended to be synonymous with "weight percent," "wt-%," etc.

The methods and compositions of the present invention may comprise, consist essentially of, or consist of the components and ingredients of the present invention as well as other ingredients described herein. As used herein, "consisting essentially of" means that the methods and compositions may include additional steps, components or ingredients, but only if the additional steps, components or ingredients do not materially alter the basic and novel characteristics of the claimed methods and compositions.

While an understanding of the mechanism is not necessary to practice the present invention and while the present invention is not limited to any particular mechanism of action, it is contemplated that, in some embodiments, the low alkaline compositions employ a combination of silicates and/or metasilicates (and optionally other alkalinity agents) and a chelant, builder and/or threshold agent as a substitute for conventional caustic compositions while still providing highly alkaline detergent compositions. Beneficially, the pH of the alkaline detergent compositions in a concentrate is less than about 11.5 reducing safety concerns associated with handling and/or transporting the low alkaline composition. While not wishing to be bound by any theory, it is believed that the particular combination of components selected for the detergent compositions of the invention, as opposed to one specific component, work synergistically to provide both efficacious detergency without the need for caustic concentrations as conventionally found in highly alkaline compositions, along with effective scale hardness control. As a result, there is no need for a separate product for detergency, including de-staining purposes, as may conventionally be provided by surfactants, additional polymers, enzymes or the like.

Detergent Compositions

According to an embodiment of the invention the detergent compositions are low alkaline. In an additional embodiment of the invention the low alkaline detergent compositions reduce scale build-up and provide enhanced protein removal from treated surfaces. In preferred embodiment of the invention the low alkaline detergent compositions substantially eliminate or completely eliminate scale build-up on treated surfaces (e.g. glasses or other ware). Without being limited to a theory of the invention, the use of non-caustic alkalinity sources, including silicates presents additional difficulties in preventing scaling on the surface of glass (and other ware). For example, silicate can also cause a film or bluing effect on the surface. Therefore, this presents additional difficult for the prevention of scaling when employing low alkaline detergent compositions.

In some embodiments, the low alkaline detergent compositions comprise, consist of and/or consist essentially of an aminocarboxylate (acid or salt), a water conditioning polymer, a builder (or secondary chelating agent), a non-caustic source of alkalinity and water. In additional embodiments, the low alkaline detergent compositions comprise, consist of and/or consist essentially of an aminocarboxylic acid (or salt), a water conditioning polymer, a builder (or secondary chelating agent), a non-caustic source of alkalinity (and optionally an additional source of alkalinity), water and additional functional ingredient(s). Unexpectedly, the low alkaline detergent compositions eliminate scaling on the treated surfaces and enhance protein removal from the treated surfaces.

Organic chelating agents have been used in various detergent compositions and cleaning compositions as builders, including phosphate-free builders. See Trilon® M Liquid, Technical Information, August 1998 (BASF Corp.), which is herein incorporated by reference in its entirety. However, according to the present invention, an aminocarboxylate is employed as a chelating agent as well as threshold agent in low alkaline detergent compositions. The beneficial cleaning efficacy of the detergent compositions results, without being limited to a particular theory of the invention, from the combined use of the aminocarboxylate, water conditioning polymer, builder (or secondary chelating agent), and non-caustic source of alkalinity (and optionally an additional source of alkalinity) while providing an alkaline detergent having a pH of less than about 11.5 in a concentrate, and between preferably about 8 and 9.5 in a use solution that effectively reduces or eliminates water hardness scaling and enhances protein removal from treated surfaces and substrates.

Aminocarboxylates

In an embodiment the detergent compositions include a chelant and/or threshold agent. In general, a chelating agent is a molecule capable of coordinating (i.e., binding) the metal ions commonly found in natural water to prevent the metal ions from interfering with the action of the other detersive ingredients of a cleaning composition. In an aspect, the chelant is an aminocarboxylic acid and/or salt, also referred to herein as an aminocarboxylate. Beneficially, aminocarboxylates may include aminocarboxylic acids and/or salts of the aminocarboxylic acids. Such materials used according to the invention do not contain phosphorus and/or contain little to no nitrilotriacetic acid (NTA) while providing effective scale inhibition in the detergent composition. In an aspect, such materials used according to the invention are biodegradable aminocarboxylates. The chelant inhibits scale build-up by chemically binding to calcium or magnesium cations, usually in a one-to-one molar ratio, to form a complex, i.e., a chelate.

In one embodiment, the aminocarboxylate used in the low alkaline detergent composition has the following structure:

wherein $R_1$ is selected from any one of H, $CH_3$, $CH_2COOH$, $CH(COOH)CH_2COOH$, $CH(CH_3)COOH$, $CH(COOH)CH_2CH_2COOH$, $CH_2CH(OH)CH_3$, $CH_2COOH$, $CH_2CH_2COOH$, and $CH_2OH$; and wherein $R_2$ is selected from any one of H, COOH, $CH_2COOH$, $CH_2OH$, $CH_2CH_2OH$, $CH_2CH_2CH_2OH$, $CH_2CH(OH)CH_3$, $CH_2CH_2N(CH_2COOH)_2$, $CH_2CH_2NHCH_2CH_2N(CH_2COOH)_2$, $CH_2CH_2NHCH(COOH)CH_2COOH$, $CH(CH_3)COOH$, $CH(COOH)CH_2CH_2COOH$, $CH(COOH)CH_2OH$, and $CH(COOH)CH_2CH_2OH$.

Useful aminocarboxylic acids according to the invention include, but are not limited to: methylglycinediacetic acid (MGDA), glutamic acid-N,N-diacetic acid (GLDA). N-hydroxyethylaminodiacetic acid, ethylenediaminetetraacetic acid (EDTA), hydroxyethylenediaminetetraacetic acid, diethylenetriaminepentaacetic acid, N-hydroxyethyl-ethylenediaminetriacetic acid (HEDTA), diethylenetriaminepentaacetic acid (DTPA), ethylenediaminesuccinic acid (EDDS), 2-hydroxyethyliminodiacetic acid (HEIDA), iminodisuccinic acid (IDS), 3-hydroxy-2-2'-iminodisuccinic acid (HIDS) and other similar acids or salts thereof having an amino group with a carboxylic acid substituent. Additional description of suitable aminocarboxylates suitable for use as chelating agents and/or builders is set forth in Kirk-Othmer, Encyclopedia of Chemical Technology, Third Edition, volume 5, pages 339-366 and volume 23, pages 319-320, the disclosure of which is incorporated by reference herein.

In an embodiment, MGDA or its acid salts and/or derivatives are employed as the aminocarboxylic acid chelant and/or threshold agent. MGDA trisodium (i.e. tetrasodium) salt is commercially-available as a 40% solution of the trisodium salt under the tradename Trilon M® (BASF Corporation). In addition, aminocarboxylates may be produced through various reactions, including those disclosed by BASF Corporation in U.S. application Ser. No. 13/050,495, filed Mar. 17, 2011, the disclosure of which is incorporated by reference herein in its entirety. MGDA has the general structure shown below:

In additional embodiments of the invention, the structure of MGDA may have a number of acidic protons replaced to neutralize or partially neutralize the structure. For example, 1, 2 or 3 of the acid groups may be neutralized or partially neutralized. In addition, the aminocarboxylate (e.g. MGDA) may be present as either enantiomer or a racemic mixture thereof.

In an aspect, the detergent compositions include from about 0.1 wt-%-15 wt-% aminocarboxylate, from about 1 wt-%-10 wt-% aminocarboxylate, from about 1 wt-%-5 wt-% aminocarboxylate, preferably from about 2 wt-%-5 wt-% aminocarboxylate. In addition, without being limited according to the invention, all ranges recited are inclusive of the numbers defining the range and include each integer within the defined range. In a further aspect, the aminocarboxylate is present at a level such that a use solution of the detergent in hard water (e.g. 17 or 20 grain water hardness) does not lead to the formation of precipitate.

In an aspect, the aminocarboxylate (chelant and threshold agent) can achieve scale control independent of the water conditioning agent (scale inhibitor) of the invention. However, it has been found that there is a beneficial synergistic effect between the chemistries in a low alkaline composition that allows scale control in concentrated low alkaline detergent compositions according to the invention. The synergy between the aminocarboxylate and the water conditioning agent allow the use of concentrated amounts of the agents providing unexpected increases in hard water scale control in the applications of use according to the invention. Beneficially, in some aspects the combination of chemistries eliminates the need for surfactants, enzymes, additional polymers and the like.

Water Conditioning Polymer

In an embodiment the detergent compositions includes a water conditioning polymer. In some aspects a water conditioning polymer is a secondary builder or scale inhibitor for the liquid detergent compositions according to the invention. Without being limited to a particular theory of the invention, the combined use of the aminocarboxylate and water conditioning polymer provide a synergistic inhibition of scale build-up on treated surfaces employing the low alkaline detergent composition.

In an aspect, the water conditioning polymer is a polyacrylate, polycarboxylate or polycarboxylic acid. Exemplary polycarboxylates that can be used as builders and/or water conditioning polymers include, but are not limited to: those having pendant carboxylate (—$CO_2^-$) groups such as acrylic homopolymers, polyacrylic acid, maleic acid, maleic/olefin copolymer, sulfonated copolymer or terpolymer, acrylic/maleic copolymer, polymethacrylic acid, acrylic acid-methacrylic acid copolymers, hydrolyzed polyacrylamide, hydrolyzed polymethacrylamide, hydrolyzed polyamidemethacrylamide copolymers, hydrolyzed polyacrylonitrile, hydrolyzed polymethacrylonitrile, and hydrolyzed acrylonitrile-methacrylonitrile copolymers. For a further discussion of water conditioning polymers, see Kirk-Othmer, Encyclopedia of Chemical Technology, Third Edition, volume 5, pages 339-366 and volume 23, pages 319-320, the disclosure of which is incorporated by reference herein.

According to an embodiment of the invention, the water conditioning polymer may be a non-phosphorus polymer. In a further embodiment, a neutralized polycarboxylic acid polymer is employed as the water conditioning polymer. An exemplary neutralized polycarboxylic acid is commercially-available as Acumer® 1000 (Rohm & Haas Company).

In an aspect, the detergent compositions include from about 0.1 wt-%-15 wt-% water conditioning polymer, from about 0.1 wt-%-10 wt-% water conditioning polymer, from about 1 wt-%-10 wt-% water conditioning polymer, preferably from about 1 wt-%-5 wt-% water conditioning polymer. In addition, without being limited according to the invention, all ranges recited are inclusive of the numbers defining the range and include each integer within the defined range. In a further aspect, the water conditioning polymer is present at a level such that a use solution of the detergent in hard water (e.g. 17 or 20 grain water hardness) does not lead to the formation of precipitate.

Builder

In an embodiment the detergent compositions includes a secondary chelating agent or a builder. In some aspects the agent is secondary to the aminocarboxylate chelating agent and is used to reduce water hardness in ware wash applications according to the invention. In an aspect of the invention, the builder may be a phosphorus-containing component. In an alternative aspect of the invention, the builder may be a phosphorus-free component.

Examples of conventional phosphorus-containing builders or chelating materials (e.g., builders) include, but are not limited to condensed phosphates, phosphonates, organic phosphonates and the like. Examples of condensed phosphates include, but are not limited to: sodium and potassium orthophosphate, sodium and potassium pyrophosphate, sodium tripolyphosphate, and sodium hexametaphosphate. Examples of phosphonates include, but are not limited to: 2-phosphonobutane-1,2,4-tricarboxylic acid (PBTC), 1-hydroxyethane-1, 1-diphosphonic acid. $CH_2C(OH)[PO(OH)_2]_2$; aminotri(methylenephosphonic acid), $N[CH_2 PO(OH)_2]_3$; aminotri(methylenephosphonate), sodium salt (ATMP), $N[CH_2 PO(ONa)_2]_3$; 2-hydroxyethyliminobis(methylenephosphonic acid), $HOCH_2CH_2 N[CH_2PO(OH)_2]_2$; diethylenetriaminepenta(methylenephosphonic acid), $(HO)_2POCH_2 N[CH_2 CH_2 N[CH_2 PO(OH)_2]_2]_2$; diethylenetriaminepenta(methylenephosphonate), sodium salt (DTPMP), $C_9 H_{(28-x)} N_3 Na_xO_{15} P_5$ (x=7); hexamethylenediamine(tetramethylenephosphonate), potassium salt, $C_{10}H_{(28-x)} N_2K_x O_{12} P_4$ (x=6); bis(hexamethylene)triamine(pentamethylenephosphonic acid), $(HO_2)POCH_2 N[(CH_2)_2N[CH_2 PO(OH)_2]_2]_2$; and phosphorus acid, $H_3PO_3$.

In an aspect, a 2-phosphonobutane-1,2,4-tricarboxylic acid is employed as the builder, sold under the tradename Bayhibit AM® and is commercially-available from Lanxess Corporation.

In an aspect, the detergent compositions include from about 0.1 wt-%-15 wt-% builder, from about 1 wt-%-10 wt-% builder, from about 1 wt-%-8 wt-% builder, preferably from about 1 wt-%-5 wt-% builder. In addition, without being limited according to the invention, all ranges recited are inclusive of the numbers defining the range and include each integer within the defined range. In a further aspect, the builder is present at a level such that a use solution of the detergent in hard water (e.g. 17 or 20 grain water hardness) does not lead to the formation of precipitate.

Alkalinity Source

In an embodiment the detergent compositions includes a non-caustic alkalinity source (and optionally an additional alkalinity source). In an aspect, the alkalinity source(s) may contain alkaline metal hydroxide or alkaline metal silicate to provide the low alkaline compositions providing concentrate compositions having a pH below about 11.5.

In an aspect, the source of non-caustic alkalinity can be any source of alkalinity that is compatible with the other components of the detergent composition and that will provide a use solution with the desired pH. One or more alkaline sources can be used to enhance cleaning of a substrate and improve soil removal performance of the detergent composition. It should be understood that the alkalinity source may be provided as part of the aminocarboxylate; that is, the aminocarboxylate provides a source of alkalinity accompanying an additional alkalinity source. In a preferred aspect of the invention, substantially similar alkalinity is provided by the detergent compositions employing an aminocarboxylate and the alkali metal silicates, as compared to a conventional caustic detergent.

In a preferred aspect, as hydroxide-based alkalinity sources (e.g. sodium hydroxide) are removed from the formulations, including raw material sources, the alkalinity source is an alkali metal silicate and does not include metasilicates due to the decreased pH of the detergent formulations according to the invention. As a result of the removal of hydroxide alkalinity sources and metasilicate alkalinity sources, the alkaline detergent composition can be formulated to provide a concentrate having a pH less than about 11.5 an a use solution preferably between about 8 and 9.5.

Examples of suitable alkalinity sources for the detergent compositions according to the invention include, but are not limited to alkali metal silicates. These include for example, lithium, sodium and potassium silicate, as well as combinations of the foregoing materials. In a preferred aspect of the invention, the alkali metal silicate is not combined with other raw materials such as alkali metal hydroxides (e.g. sodium hydroxide) and therefore does not generate alkali metal metasilicates prior to or in the process of making the non-caustic detergent composition according to the invention.

In an aspect of the invention, the alkali metal silicates may be added to the composition in any form known in the art, including as solid beads, dissolved in an aqueous solution, or a combination thereof. Commercial sodium silicates are available in both powdered and liquid forms. The powdered forms include both amorphous and crystalline powders in either hydrated or anhydrous form. The aqueous liquids are available with viscosities ranging from 0.5 to 600,000 centipoise at 20° C. Potassium silicates are sold either as a glass or an aqueous liquid. The synthetic lithium silicates typically are generally sold only as liquids. The more common commercially available sodium silicates vary in $Na_2O/SiO_2$ ratio from about 2:1 to about 1:4.

The solid forms of alkali metal silicates are generally classified by particle-size range and $Na_2O/SiO_2$ ratio. The aqueous solutions are identified by any combination of density/specific gravity, alkali:silica ratio, and viscosity. Typically, the aqueous solutions are differentiated on the basis of specific gravity and $Na_2O/SiO_2$ ratio. Concentrated solutions of highly alkali sodium silicates are quite sticky or tacky. Conversely, concentrated solutions of highly siliceous sodium silicate show little tack but are plastic enough to form into balls which show a surprising elasticity.

The liquid products which are readily available on a commercial scale include $M_2O:SiO_2$ ratios from about 1:1.5 to 1:3,8 for sodium silicate and about 1:1.5 to about 1:2.5 for potassium silicate with a water content from about 45 to about 75 wt % based upon the weight of the silicate and the water. Additional description of various commercially available alkali metal silicates is set forth in U.S. application Ser. No. 13/268,488, the entire contents of which are herein incorporated by reference.

In addition to a first alkalinity source, such as the preferred sodium silicates, the detergent composition may comprise a secondary non-caustic alkalinity source. Examples of useful secondary alkaline sources include, but are not limited to: additional metal salts, such as carbonates such as sodium or potassium carbonate, bicarbonate, sesquicarbonate; metal borates such as sodium or potassium borate; and ethanolamines and amines.

In an aspect of the invention, the detergent composition does not include alkali metal carbonates, alkali metal hydroxides, alkali metal salts, alkali metal metasilicates and/or mixtures thereof in its final concentrate or use solution. In a particular aspect, the concentrate or use solution of the detergent composition does not include any alkali metal hydroxide, such as sodium hydroxide, As a result, the compositions are substantially-free of caustic. Preferably, the compositions are free of caustic.

In an aspect, the detergent compositions include from about 5 wt-%-80 wt-% alkalinity, from about 10 wt-%-80 wt-% alkalinity, from about 10 wt-%-70 wt-% alkalinity, from about 10 wt-%-60 wt-% alkalinity, preferably from about 10 wt-%-50 wt-% alkalinity. In addition, without being limited according to the invention, all ranges recited are inclusive of the numbers defining the range and include each integer within the defined range.

The alkalinity source is provided in a sufficient amount to maintain an alkaline pH in a use solution in order to provide sufficient detergency properties. An effective amount of one or more alkalinity sources should be considered as an amount that provides a concentrate composition having a pH of less than about 11.5. In a further aspect an effective amount of one or more alkalinity sources should be considered as an amount that provides a use composition having a pH of at least about 8, preferably between about 8 and 9.5. When the use composition has a pH of between about 8 and about 10, it can be considered mildly alkaline, and when the pH is greater than about 12, the use composition can be considered caustic. Particularly, the pH of the use solution of the detergent composition is between about 8 and about 9.5, preferably between about 8.5 and about 9.5. In addition, without being limited according to the invention, all ranges recited are inclusive of the numbers defining the range and include each integer within the defined range. If the pH of the use solution is too low, for example, below approximately 8, the use solution may not provide adequate detergency properties. If the pH of the use solution is too high, for example, above approximately 12-13, the use solution may be too alkaline and attack or damage the surface to be cleaned as well as require additional safety considerations for transport and/or handling of the highly alkaline detergent.

Beneficially, the use of an aminocarboxylate chelating agents with the non caustic-based alkalinity provides a less concentrated alkaline detergent. In some aspects, the low alkaline detergent composition has a pH less than about 11.5 (concentrate) providing improved safety with respect to contact and transportation, for example. The removal of caustic from the detergent compositions employing an aminocarboxylate provides decreased pH in comparison to a caustic detergent having a pH greater than about 12, greater than about 13, or about 14. According to the invention, the use of silicates with the aminocarboxylate unexpectedly provide increased alkalinity as both provide alkalinity sources, along with the beneficial chelating and threshold efficacy for a detergent composition, without the use of caustic.

Water

In an embodiment the detergent compositions includes water. Preferably, the detergent compositions are formulated into liquid compositions. The water employed in the compositions can be from a variety of sources and may include hard and/or softened or treated water.

In an aspect, the detergent compositions include from about 20 wt-%-80 wt-% water, from about 20 wt-%-60 wt-% water, from about 30 wt-%-80 wt-% water, from about 40 wt-%-80 wt-% water, preferably from about 50 wt-%-70 wt-% water. In addition, without being limited according to the invention, all ranges recited are inclusive of the numbers defining the range and include each integer within the defined range.

Additional Functional Ingredients

The components of the detergent composition can further be combined with various functional components suitable for use in ware wash applications. In some embodiments, the detergent composition including the aminocarboxylate, water, alkalinity source, builder and water conditioning polymer make up a large amount, or even substantially all of the total weight of the detergent composition. For example, in some embodiments few or no additional functional ingredients are disposed therein.

In other embodiments, additional functional ingredients may be included in the detergent compositions. The functional ingredients provide desired properties and functionalities to the low alkaline detergent compositions. For the purpose of this application, the term "functional ingredient" includes a material that when dispersed or dissolved in a use and/or concentrate solution, such as an aqueous solution, provides a beneficial property in a particular use. Some particular examples of functional materials are discussed in more detail below, although the particular materials discussed are given by way of example only, and that a broad variety of other functional ingredients may be used. For example, many of the functional materials discussed below relate to materials used in cleaning, specifically ware wash applications. However, other embodiments may include functional ingredients for use in other applications.

In preferred embodiments, the low alkaline detergent compositions do not include enzymes. In preferred embodiments, the low alkaline detergent compositions do not include chlorine or a chlorine source, such as various bleaching agents. In a still more preferred aspect, the low alkaline detergent compositions do not include bleach or bleaching agents. In further preferred embodiments, the low alkaline detergent compositions do not include surfactants. In still further preferred embodiments, the low alkaline detergent compositions do not include additional polymers. In preferred aspects of the invention, the low alkaline detergent composition is a liquid composition that does not include enzymes, chlorine or a chlorine source, surfactants and/or optionally additional polymers.

In a preferred embodiment, the low alkaline detergent compositions include a sanitizer and/or are used with a sanitizer for use of the compositions at low temperatures (e.g wash temperatures below about 140° F.). In other embodiments, the low alkaline detergent compositions may include polymers that are defoaming agents, anti-redeposition agents, bleaching agents, solubility modifiers, dispersants, rinse aids, metal protecting agents, stabilizing agents, builders, corrosion inhibitors, sanitizing agents or antimicrobial agents, additional builders and/or chelating agents, fragrances and/or dyes, rheology modifiers or thickeners, hydrotropes or couplers, buffers, solvents and the like. In an aspect, the low alkaline detergent compositions include a food grade rinse aid, including for example a GRAS product. The term "generally recognized as safe" or "GRAS," as used herein refers to components classified by the Food and Drug Administration as safe for direct human food consumption or as an ingredient based upon current good manufacturing practice conditions of use, as defined for example in 21 C.F.R. Chapter 1, § 170.38 and/or 570,38.

Defoaming Agents

A defoaming agent for reducing the stability of foam may also be included in the ware washing detergent composition. Examples of defoaming agents include, but are not limited to: ethylene oxide/propylene block copolymers such as those available under the name Pluronic N-3, silicone compounds such as silica dispersed in polydimethylsiloxane, polydimethylsiloxane, and functionalized polydimethylsiloxane; fatty amides, hydrocarbon waxes, fatty acids, fatty esters, fatty alcohols, fatty acid soaps, ethoxylates, mineral oils, and polyethylene glycol esters. A discussion of defoaming agents may be found, for example, in U.S. Pat. Nos. 3,048,548, 3,334,147, and 3,442,242, the disclosures of which are incorporated herein by reference. When the concentrate includes a defoaming agent, the defoaming agent can be provided in an amount of between approximately 0.0001% and approximately 10% by weight, between approximately 0.001% and approximately 5% by weight, or between approximately 0.01% and approximately 1.0% by weight. All ranges recited are inclusive of the numbers defining the range and include each integer within the defined range.

Anti-Redeposition Agents

The detergent composition can include an anti-redeposition agent for facilitating sustained suspension of soils in a cleaning solution and preventing the removed soils from being redeposited onto the substrate being cleaned. Examples of suitable anti-redeposition agents include, but are not limited to: polyacrylates, styrene maleic anhydride copolymers, cellulosic derivatives such as hydroxyethyl cellulose, hydroxypropyl cellulose and carboxymethyl cellulose. When the concentrate includes an anti-redeposition agent, the anti-redeposition agent can be included in an amount of between approximately 0.5% and approximately 10% by weight, and between approximately 1% and approximately 5% by weight. All ranges recited are inclusive of the numbers defining the range and include each integer within the defined range.

Stabilizing Agents

The detergent composition may also include stabilizing agents. Examples of suitable stabilizing agents include, but are not limited to: borate, calcium/magnesium ions, propylene glycol, and mixtures thereof. The concentrate need not include a stabilizing agent, but when the concentrate includes a stabilizing agent, it can be included in an amount that provides the desired level of stability of the concentrate. Exemplary ranges of the stabilizing agent include up to approximately 20% by weight, between approximately 0.05% and approximately 15% by weight, and between approximately 0.1% and approximately 10% by weight. All ranges recited are inclusive of the numbers defining the range and include each integer within the defined range.

Glass and Metal Corrosion Inhibitors

The detergent composition can include a metal corrosion inhibitor in an amount up to approximately 50% by weight, between approximately 0.01% and approximately 40% by weight, or between approximately 0.1% and approximately 30% by weight. All ranges recited are inclusive of the numbers defining the range and include each integer within the defined range.

The corrosion inhibitor is included in the detergent composition in an amount sufficient to provide a use solution that exhibits a rate of corrosion and/or etching of glass that is less than the rate of corrosion and/or etching of glass for an otherwise identical use solution except for the absence of the corrosion inhibitor. It is expected that the use solution will include at least approximately 6 parts per million (ppm) of the corrosion inhibitor to provide desired corrosion inhibition properties. It is expected that larger amounts of corrosion inhibitor can be used in the use solution without deleterious effects. The use solution can include between approximately 6 ppm and approximately 300 ppm of the corrosion inhibitor, and between approximately 20 ppm and approximately 200 ppm of the corrosion inhibitor. Examples of suitable corrosion inhibitors include, but are not limited to: a combination of a source of aluminum ion and a source of zinc ion, as well as an alkaline metal silicate or hydrate thereof.

The corrosion inhibitor can refer to the combination of a source of aluminum ion and a source of zinc ion. The source of aluminum ion and the source of zinc ion provide aluminum ion and zinc ion, respectively, when the solid detergent composition is provided in the form of a use solution, The amount of the corrosion inhibitor is calculated based upon the combined amount of the source of aluminum ion and the source of zinc ion. Anything that provides an aluminum ion in a use solution can be referred to as a source of aluminum ion, and anything that provides a zinc ion when provided in a use solution can be referred to as a source of zinc ion. It is not necessary for the source of aluminum ion and/or the source of zinc ion to react to form the aluminum ion and/or the zinc ion. Aluminum ions can be considered a source of aluminum ion, and zinc ions can be considered a source of zinc ion. The source of aluminum ion and the source of zinc ion can be provided as organic salts, inorganic salts, and mixtures thereof.

Exemplary sources of aluminum ion include, but are not limited to: aluminum salts such as sodium aluminate, aluminum bromide, aluminum chlorate, aluminum chloride, aluminum iodide, aluminum nitrate, aluminum sulfate, aluminum acetate, aluminum formate, aluminum tartrate, aluminum lactate, aluminum oleate, aluminum bromate, aluminum borate, aluminum potassium sulfate, and aluminum zinc sulfate. Exemplary sources of zinc ion include, but are not limited to: zinc salts such as zinc chloride, zinc sulfate, zinc nitrate, zinc iodide, zinc thiocyanate, zinc fluorosilicate, zinc dichromate, zinc chlorate, sodium zincate, zinc gluconate, zinc acetate, zinc benzoate, zinc citrate, zinc lactate, zinc formate, zinc bromate, zinc bromide, zinc fluoride, zinc fluorosilicate, and zinc salicylate.

Silicates can be included in the detergent composition to provide for metal protection but are additionally known to provide alkalinity and additionally function as anti-redeposition agents. Exemplary silicates include, but are not limited to: sodium silicate and potassium silicate. The detergent composition can be provided without silicates, but when silicates are included, they can be included in amounts that provide for desired metal protection. The concentrate can include silicates in amounts of at least approximately 1% by weight, at least approximately 5% by weight, at least approximately 10% by weight, and at least approximately 15% by weight. In addition, in order to provide sufficient room for other components in the concentrate, the silicate component can be provided at a level of less than approximately 35% by weight, less than approximately 25% by weight, less than approximately 20% by weight, and less than approximately 15% by weight.

Thickeners

The detergent compositions can include a rheology modifier or a thickener in amounts suitable for adjusting the thickness of a particular composition to particular viscosity, such amounts which shall vary. A rheology modifier or a thickener can be provided in an amount of between approximately 0.0001% and approximately 10% by weight, between approximately 0.001% and approximately 10% by weight, or between approximately 0.01% and approximately 10% by weight. All ranges recited are inclusive of the numbers defining the range and include each integer within the defined range.

The rheology modifier may provide the following functions: increasing the viscosity of the compositions; increasing the particle size of liquid use solutions when dispensed through a spray nozzle; providing the use solutions with vertical cling to surfaces; providing particle suspension within the use solutions; or reducing the evaporation rate of the use solutions. Examples of suitable thickeners or heology modifiers are polymeric thickeners including, but not limited to: polymers or natural polymers or gums derived from plant or animal sources. Such materials may be polysaccharides such as large polysaccharide molecules having substantial thickening capacity. Thickeners or rheology modifiers also include clays.

A substantially soluble polymeric thickener can be used to provide increased viscosity or increased conductivity to the use compositions. Examples of polymeric thickeners for the aqueous compositions of the invention include, but are not limited to: carboxylated vinyl polymers such as polyacrylic acids and sodium salts thereof, ethoxylated cellulose, polyacrylamide thickeners, cross-linked, xanthan compositions, sodium alginate and algin products, hydroxypropyl cellulose, hydroxyethyl cellulose, and other similar aqueous thickeners that have some substantial proportion of water solubility. Examples of suitable commercially available thickeners include, but are not limited to: Acusol®, available from Rohm & Haas Company, Philadelphia, Pa.; and Carbopol®, available from B.F. Goodrich, Charlotte, N.C. Additional examples of suitable polymeric thickeners include, but not limited to: polysaccharides.

An example of a particularly suitable polysaccharide includes, but is not limited to, xanthans. Such xanthan polymers are preferred due to their high water solubility, and great thickening power. Low concentrations of the gum have relatively high viscosities which permit it to be used economically. Xanthan gum solutions exhibit high pseudo plasticity, i.e. over a wide range of concentrations, rapid shear thinning occurs that is generally understood to be instantaneously reversible. Non-sheared materials have viscosities that appear to be independent of the pH and independent of temperature over wide ranges. Preferred xanthan materials include cross-linked xanthan materials. Xanthan polymers can be cross-linked with a variety of known covalent reacting crosslinking agents reactive with the hydroxyl functionality of large polysaccharide molecules and can also be cross-linked using divalent, trivalent or polyvalent metal ions. Such cross-linked xanthan gels are disclosed in U.S. Pat. No. 4,782,901, which is herein incorporated by reference. Suitable crosslinking agents for xanthan materials include, but are not limited to: metal cations such as $Al^{+3}$, $Fe^{+3}$, $Sb^{+3}$, $Zr^{+4}$ and other transition metals.

Rinse Aids

The detergent composition can optionally include a rinse aid composition, for example a rinse aid formulation containing a wetting or sheeting agent combined with other optional ingredients in a solid composition made using the binding agent. The rinse aid components are capable of reducing the surface tension of the rinse water to promote sheeting action and/or to prevent spotting or streaking caused by beaded water after rinsing is complete, for example in ware washing processes. Examples of sheeting agents include, but are not limited to: poly ether compounds prepared from ethylene oxide, propylene oxide, or a mixture in a homopolymer or block or heteric copolymer structure. Such polyether compounds are known as polyalkylene oxide polymers, polyoxyalkylene polymers or polyalkylene glycol polymers. Such sheeting agents require a region of relative hydrophobicity and a region of relative hydrophilicity to provide surfactant properties to the molecule. Additional disclosure of suitable rinse aids is provided in U.S. patent application Ser. No. 13/209,719, which is herein incorporated by reference in its entirety.

Exemplary ranges of rinse aids include up to approximately 20% by weight, between approximately 0.01% and approximately 15% by weight, and between approximately 0.1% and approximately 10% by weight. All ranges recited are inclusive of the numbers defining the range and include each integer within the defined range.

Sanitizers/Anti-Microbial Agents

The detergent composition can optionally include and/or be used in a ware wash application with a sanitizing composition (or antimicrobial agent). Sanitizing agents, also known as antimicrobial agents, are chemical compositions that can be used to prevent microbial contamination and deterioration of material systems, surfaces, etc. Generally, these materials fall in specific classes including phenolics, halogen compounds, quaternary ammonium compounds, metal derivatives, amines, alkanol amines, nitro derivatives, anilides, organosulfur and sulfur-nitrogen compounds and miscellaneous compounds.

The given antimicrobial agent, depending on chemical composition and concentration, may simply limit further proliferation of numbers of the microbe or may destroy all or a portion of the microbial population. The terms "microbes" and "microorganisms" typically refer primarily to bacteria, virus, yeast, spores, and fungus microorganisms. In use, the antimicrobial agents are typically formed into a solid functional material that when diluted and dispensed, optionally, for example, using an aqueous stream forms an aqueous disinfectant or sanitizer composition that can be contacted with a variety of surfaces resulting in prevention of growth or the killing of a portion of the microbial population. Sanitizing compounds capable of liberating an active halogen species, such as $Cl_2$, $Br_2$, —OCl— and/or —OBr—, or the like, under conditions typically encountered during the cleansing process may be used. Examples of suitable halogen-releasing compounds include, but are not limited to: chlorine-containing compounds such as chlorine, a hypochlorite or chloramines, and alkali metal dichloroisocyanurates, alkali metal hypochlorites, monochloramine, and dichloroamine. Encapsulated chlorine sources may also be used to enhance the stability of the chlorine source in the composition (see, for example, U.S. Pat. Nos. 4,618,914 and 4,830,773, the disclosures of which are incorporated by reference herein in their entirety).

Examples of suitable antimicrobial agents include, but are not limited to, phenolic antimicrobials such as pentachlorophenol; orthophenylphenol; chloro-p-benzylphenols;

p-chloro-m-xylenol; quaternary ammonium compounds such as alkyl dimethylbenzyl ammonium chloride; alkyl dimethylethylbenzyl ammonium chloride; octyl decyldimethyl ammonium chloride; dioctyl dimethyl ammonium chloride; and didecyl dimethyl ammonium chloride. Examples of suitable halogen containing antibacterial agents include, but are not limited to: sodium trichloroisocyanurate, sodium dichloro isocyanate (anhydrous or dihydrate), iodine-poly(vinylpyrolidinone) complexes, bromine compounds such as 2-bromo-2-nitropropane-1,3-diol, and quaternary antimicrobial agents such as benzalkonium chloride, didecyldimethyl ammonium chloride, choline diiodochloride, and tetramethyl phosphonium tribromide. Other antimicrobial compositions such as hexahydro-1,3,5-tris(2-hydroxyethyl)-s-triazine, dithiocarbamates such as sodium dimethyldithiocarbamate, percarbonate, iodine solutions, and a variety of other materials are known in the art for their antimicrobial properties.

Exemplary ranges of antimicrobial agents include up to approximately 30% by weight, between approximately 0.01% and approximately 20% by weight, and between approximately 0.1% and approximately 15% by weight. All ranges recited are inclusive of the numbers defining the range and include each integer within the defined range.

Dyes and Fragrances

Various dyes, odorants including perfumes, and other aesthetic enhancing agents may also be included in the cleaning composition. Dyes may be included to alter the appearance of the composition, as for example, any of a variety of FD&C dyes, D&C dyes, and the like. Additional suitable dyes include Acid Red, Direct Blue 86 (Miles), Fastusol Blue (Mobay Chemical Corp.), Acid Orange 7 (American Cyanamid), Basic Violet 10 (Sandoz), Acid Yellow 23 (GAF), Acid Yellow 17 (Sigma Chemical), Sap Green (Keystone Aniline and Chemical), Metanil Yellow (Keystone Aniline and Chemical), Acid Blue 9 (Hilton Davis), Sandolan Blue/Acid Blue 182 (Sandoz), Hisol Fast Red (Capitol Color and Chemical), Fluorescein (Capitol Color and Chemical), Acid Green 25 (BASF), Pylakor Acid Bright Red (Pylam), and the like.

Fragrances or perfumes that may be included in the compositions include, for example, terpenoids such as citronellol, aldehydes such as amyl cinnamaldehyde, a jasmine such as C1S-jasmine or jasmal, vanillin, and the like.

Exemplary ranges of dyes and/or fragrances include up to approximately 20% by weight, between approximately 0.01% and approximately 15% by weight, and between approximately 0.1% and approximately 10% by weight. All ranges recited are inclusive of the numbers defining the range and include each integer within the defined range.

Embodiments

Exemplary ranges of the concentrated low alkaline detergent compositions according to the invention are shown in Table 1 in weight percentage of the liquid detergent compositions. Sanitizers that are employed with the concentrated low alkaline detergent compositions according to the invention for use at low temperatures may be formulated into the composition or provided separately from the detergent compositions. In a further aspect, rinse aids may be further employed with the concentrated low alkaline detergent compositions, which may be formulated into the composition or provided separately from the detergent compositions. In a preferred aspect, the use of rinse aids and/or sanitizers are provided separately from the detergent compositions.

TABLE 1

| Material | First Exemplary Range wt-% | Second Exemplary Range wt-% | Third Exemplary Range wt-% | Fourth Exemplary Range wt-% |
|---|---|---|---|---|
| Water | 20-80 | 30-80 | 40-80 | 50-70 |
| Aminocarboxylate | 0.1-15 | 1-10 | 1-5 | 2-5 |
| Non-Caustic Alkalinity Source | 5-80 | 10-80 | 10-70 | 10-50 |
| Water Conditioning Polymer | 0.1-15 | 0.1-10 | 1-10 | 1-5 |
| Builder | 0.1-15 | 0.1-10 | 1-8 | 1-5 |
| Additional Functional Ingredients | 0-25 | 0-20 | 0-10 | 0-5 |

In some aspects the ratio of the aminocarboxylate to the water conditioning polymer to the builder is in a ratio of from about 1:1:1 to about 5:1:10, preferably from about 1:1:1 to about 2.5:1:5. In some aspects the ratio of the aminocarboxylate to the water conditioning polymer is from about 1:5 to about 5:1, preferably from about 1:3 to about 3:1, preferably from about 1:2.5 to about 2.5:1, preferably from about 1:2 to about 2:1, or about 1:1. In a preferred aspect, the ratio of the aminocarboxylate to the water conditioning polymer is about 2:1. In some aspects the ratio of the aminocarboxylate to the builder is from about 1:10 to about 10:1, preferably from about 1:5 to about 5:1, preferably from about 1:3 to about 3: preferably from about 1:2 to about 2:1, or about 1:1. In some aspects the ratio of the water conditioning agent to the builder is from about 1:10 to about 10:1, preferably from about 1:5 to about 5:1, preferably from about 1:3 to about 3:1, preferably from about 1:2 to about 2:1, or about 1:1. In some aspects the ratio of the aminocarboxylate to the alkalinity source is from about 1:5 to about 1:100, preferably from about 1:5 to about 1:10. in addition, without being limited according to the invention, all ranges for the ratios recited are inclusive of the numbers defining the range and include each integer within the defined range of ratios.

The detergent compositions may include concentrate compositions or may be diluted to form use compositions. In general, a concentrate refers to a composition that is intended to be diluted with water to provide a use solution that contacts an object to provide the desired cleaning, rinsing, or the like. The detergent composition that contacts the articles to be washed can be referred to as a concentrate or a use composition (or use solution) dependent upon the formulation employed in methods according to the invention. It should be understood that the concentration of the aminocarboxylate, water conditioning agent, alkalinity, water and other optional functional ingredients in the detergent composition will vary depending on whether the detergent composition is provided as a concentrate or as a use solution.

A use solution may be prepared from the concentrate by diluting the concentrate with water at a dilution ratio that provides a use solution having desired detersive properties. The water that is used to dilute the concentrate to form the use composition can be referred to as water of dilution or a diluent, and can vary from one location to another. The typical dilution factor is between approximately 1 and approximately 10,000 but will depend on factors including water hardness, the amount of soil to he removed and the like. In an embodiment, the concentrate is diluted at a ratio of between about 1:5 or about 1:10 and about 1:10,000 concentrate to water. Particularly, the concentrate is diluted at a ratio of between about 1:100 and about 1:5,000 concentrate to water. More particularly, the concentrate is diluted at a ratio of between about 1:100 and about 1:2,500 or between about 1:250 and about 1:2,000 concentrate to water.

In an aspect of the invention, a use solution of the low alkaline detergent composition has between about 1 ppm to about 250 ppm aminocarboxylate, between about 1 ppm to about 250 ppm water conditioning polymer, between about 1 ppm to about 250 ppm builder, and between 10 ppm to about 1,000 ppm alkalinity source. In a preferred aspect of the invention, a use solution of the phosphorus-free detergent composition has between about 1 ppm to about 100 ppm aminocarboxylate, between about 1 ppm to about 100 ppm water conditioning polymer, between about 1 ppm to about 100 ppm builder, and between 5 ppm to about 500 ppm alkalinity source. In a still further preferred aspect of the invention, a use solution of the phosphorus-free detergent composition has between about 1 ppm to about 25 ppm aminocarboxylate, between about 1 ppm to about 25 ppm water conditioning polymer, between about 1 ppm to about 25 ppm builder, and between 5 ppm to about 100 ppm alkalinity source. In addition, without being limited according to the invention, all ranges recited are inclusive of the numbers defining the range and include each integer within the defined range.

In an aspect of the invention, the detergent composition preferably provides efficacious cleaning at low use dilutions, i.e., require less volume to clean effectively. In an aspect, a concentrated liquid detergent composition may be diluted in water prior to use at dilutions ranging from about 1/16 oz./gal. to about 2 oz./gal. or more. A detergent concentrate that requires less volume to achieve the same or better cleaning efficacy and provides hardness scale control and/or other benefits at low use dilutions is desirable.

Methods Employing the Present Compositions

The methods of employing the low alkaline detergent compositions are particularly suited for use in closed systems, e.g. dish or ware washing systems for cleaning, sanitizing and/or disinfecting articles and surfaces. According to an embodiment of the invention a method of low temperature ware washing is provided to clean treated surfaces. In an embodiment the method can result in reduced hard water scaling on an article or surface exposed to water hardness. The methods of the invention are particularly suited for commercial applications to enable the use of lower temperature wash applications, beneficially reducing energy expenditures for heating wash waters.

The method includes contacting an article or surface with a detergent composition or a detergent use composition according to the invention to wash the surface. The method can contact the liquid to any of a variety of surfaces or objects including surfaces or articles including those made of glass, ceramic, plastic, porcelain, aluminum, or the like.

The phrase "washing a surface with a detergent wash solution (or a use solution or a detergent composition)" refers to the circulation of a detergent composition solution to remove substantially all soil from the treated surfaces (e.g. ware) and to keep that soil suspended or dissolved. In an embodiment, this step may be conducted where the temperature of the rinse water is up to about 140° F., preferably in the range of 100° F. to 140° F., preferably in the range of 110° F. to 140° F., and most preferably in the range of 120° F. to 140° F. As referred to herein, "low temperature" refers to those rinse water temperatures below about 140° F. For example, conventional rinse temperature for ware washing occurs above 140° F., such as from about 140° F. to about 190° F., particularly between about 145° F. to about 180° F.

In an aspect, the methods of the invention employing a low temperature further employ a sanitizer.

In an embodiment, the present invention includes a method of cleaning an article or surface while also reducing scale hardness build-up on the article or surface. This method can include: providing the phosphorus-free detergent composition including an aminocarboxylate, water conditioning agent, source of alkalinity, water and optionally additional functional ingredients; forming an aqueous composition of the phosphorus-free detergent composition to dilute a liquid concentrate; and contacting the aqueous composition to an article to clean the article and reduce scale hardness build-up on the article.

Contacting can include any of numerous methods for applying a composition, such as spraying the composition, immersing the object in the composition, or a combination thereof. A concentrate or use concentration of a composition of the present invention can be applied to or brought into contact with an article by any conventional method or apparatus for applying a cleaning composition to an object. For example, the object can be wiped with, sprayed with, and/or immersed in the composition, or a use solution made from the composition. The composition can be sprayed, or wiped onto a surface; the composition can be caused to flow over the surface, or the surface can be dipped into the composition. Contacting can be manual or by machine.

Before contacting an article or surface, a concentrate detergent composition may be first diluted with water at the location of use to provide the use solution. When the composition is used in an automatic ware washing or dishwashing machine, it is expected that that the location of use will be inside the automatic ware washing machine. Depending on the machine, the composition may be provided in a unit dose form or in a multi-use form. In larger ware washing machines, a large quantity of composition may be provided in a compartment that allows for the release of a single dose amount of the composition for each wash cycle. Such a compartment may be provided as part of the ware washing machine or as a separate structure connected to the ware washing machine, The detergent composition may also be dispensed from a spray-type dispenser, such as that disclosed in U.S. Pat. Nos. 4,826,661, 4,690,305, 4,687,121, 4,426,362 and in U.S. Pat. Nos. Reissue 32,763 and 32,818, the disclosures of which are incorporated by reference herein. Briefly, a spray-type dispenser functions by impinging a water spray upon an exposed surface of the composition, and then immediately directing the use solution out of the dispenser to a storage reservoir or directly to a point of use. if necessary, in some embodiments, when used, the product may be removed from the packaging and inserted into the dispenser.

The methods of the invention may further employ one or more rinse steps for the treated articles or surfaces. In an aspect, the commercial use of the phosphorus-free detergent compositions at low temperatures preferably include a rinse step employing a rinse aid, including for example, the disclosure of using rinse aids set forth in U.S. patent application Ser. No. 13/480,031, which is herein incorporated by reference in its entirety. In the alternative, consumer use of the phosphorus-free detergent compositions would not require the use of a rinse aid as this step is employed using a clean water source. In a further aspect, in consumer use of the phosphorus-free detergent composition at normal or elevated temperatures (e.g. above about 140° F.) does not require the use of a sanitizer.

All publications and patent applications in this specification are indicative of the level of ordinary skill in the art to which this invention pertains. All publications and patent applications are herein incorporated by reference to the same extent as if each individual publication or patent application was specifically and individually indicated as incorporated by reference.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims.

The materials used in the following Examples are provided herein:

Trilon M®: methyl glycine diacetic acid/MGDA., trisodium salt/$Na_3MGDA$ (solution in water) (aminocarboxylic acid chelant and threshold agent), commercially-available from BASF Corporation.

Bayhibit® AM: 2-phosphono-1,2,4-butanetricarboxylic acid (phosphonbutane tricarboxylic acid (PBTC) chelant/scale inhibitor/corrosion inhibitor), commercially-available from Lanxess Corporation.

Acumer® 1000: a neutralized polycarboxylic acid, commercially-available from Rohm & Haas.

Acusol® 425N: a neutralized acrylic acid copolymer threshold agent and scale inhibitor, commercially-available as a 50% solution from Rohm & Haas.

Belclene® 810: a polymaleic acid terpolymer, commercially-available from BWA Water Additives.

Additional materials commercially-available from multiple sources include: sodium hydroxide (50%), RU silicate (a sodium silicate), sucrose and softened water.

Example 1

A liquid detergent composition according to the invention was compared to a control composition containing caustic shown below in Table 2. The experimental formula (EXP1) according to the invention was calculated to have the same percent actives water conditioning polymer (Acumer 1000) as the Control formula at the time of the experiment.

TABLE 2

| Description | Control | EXP1 |
| --- | --- | --- |
| Softened Water | 20-80 | 20-80 |
| Trilon M (40%) | 0 | 1-5 |
| Bayhibit AM (50%) | 1-5 | 1-5 |
| Sodium Hydroxide (50%) | 25-60 | 1-10 |
| RU Silicate (50%) | 0 | 10-20 |
| Acumer 1000 (48%) | 0.1-5 | 0.1-5 |

Beneficially, the EXP1 formulation provides a caustic-free, liquid detergent composition. The amount of sodium hydroxide formulated in the EXP1 formulation reacts with the sodium silicate to form a sodium silicate solution and neutralizes all sodium hydroxide from the formulation. As a result, the EXP1 formulation is caustic-free high alkalinity detergent composition that beneficially provides ware wash efficacy when combined with the aminocarboxylate Trilon M.

Example 2

The experimental formula (EXP1) and Control according to Example 1 were further evaluated to determine the impact of removal of caustic from the formulation on the cleaning efficacy and threshold effect with regard to scale build-up. A 100 cycle glass cleaning experiment was performed using six 10 oz. Libby glasses and a Cambro Newport plastic tumbler on a ES-2000 ware wash machine employing 17 grain water (hard water source). Initially the glasses were prepared using a cleaning cycle to completely remove all film and foreign material from the glass surface.

Figure 1:
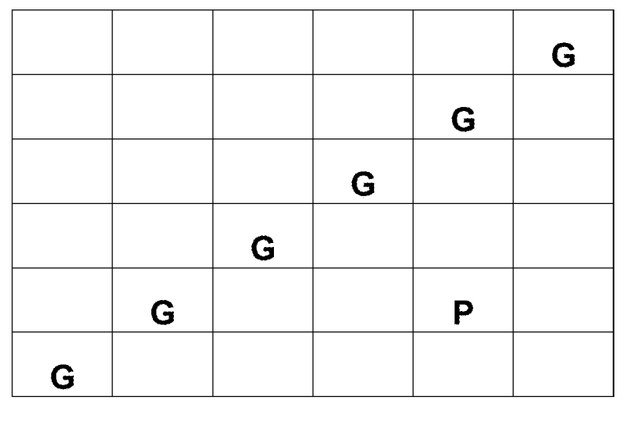
FIG. 1 shows a diagram of the ware wash machine rack employed in Example 2, showing the orientation of the six clean glasses (G=glass tumblers) and a clean plastic tumbler (P=plastic tumbler) arranged therein.

The ware wash machine controller was set to automatically dispense the indicated amount of detergent into the wash tank. Six clean glasses (G=glass tumblers) and a clean plastic tumbler (P=plastic tumbler) were placed in a Raburn rack (see FIG. 1 for arrangement) and the rack was placed inside the dishmachine.

The ware wash machine automatically dispensed into the ware wash machine the detergent compositions to achieve the desired concentration and maintain the initial concentration. After 100 wash cycles, the glasses were dried overnight and then the film accumulation using a strong light source was evaluated. The film ratings are based upon the following measurement scale: (1) no film; (2) trace amount of film that is barely visible under intense spot light conditions, but is not noticeable if the glass is held up to a fluorescent light source; (3) light film when held up to a fluorescent light source; (4) medium film, glass appears hazy when held up to a fluorescent light source; and (5) heavy film, glass appears cloudy when held up to a fluorescent light source.

The light box test standardizes the evaluation of the glasses run in the 100 cycle test. The light box test is based on the use of an optical system including a photographic camera, a light box, a light source and a light meter. The system is controlled by a computer program (Spot Advance and Image Pro Plus). To evaluate the glasses after the 100 cycle test, each glass was placed on the light box resting on its side and the intensity of the light source was adjusted to a predetermined value using a light meter. The conditions of the 100 cycle test were entered into the computer. A picture of the glass was taken with the camera and saved on the computer for analysis by the program. The picture was analyzed using the upper half of the glass in order to avoid the gradient of darkness on the film from the top of the glass to the bottom of the glass, based on the shape of the glass.

Generally, a lower light box rating indicates that more light was able to pass through the glass. Thus, the lower the light box rating, the more effective the composition was at preventing scaling on the surface of the glass. Light box evaluation of a clean, unused glass has a light box score of approximately 12,000 which corresponds to a score of 72,000 for the sum of 6 glasses.

The approximate temperature range of the 100 cycle test was <120° F., providing a stable low temperature range for ware washing, according to the methods of the invention. The use concentration of the liquid detergent was 1000 ppm. The sum of the light box score for the control was 70,809, with a light box score for the plastic tumbler of 32,712. This gives a sum of 103,521 for the glasses and the plastic tumbler combined. For EXP1, the light box score was 84,967, with a light box score for the plastic tumbler of 31,809. This gives a sum of 116,776 for the glasses and the plastic tumbler combined.

The results demonstrate that EXP1 according to the invention providing a caustic-free liquid detergent additionally provide substantially-similar cleaning benefits and reducing film on the treated surfaces as caustic compositions. The light box scores are within the range of acceptable results due to the sensitivity of the light box readings, as no visible difference it detected between the 2 sets of glasses.

Example 3

Additional experimental formulas to provide caustic-free detergent compositions were evaluated using the methods of Example 2. The compositions are shown in Table 3.

TABLE 3

| Description | EXP1 | EXP2 | EXP3 | EXP4 |
| --- | --- | --- | --- | --- |
| Softened Water | 20-80 | 20-80 | 20-80 | 20-80 |
| Trilon M (40%) | 1-5 | 1-5 | 1-5 | 1-5 |
| Bayhibit AM (50%) | 1-5 | 0 | 0 | 0 |
| Sodium Hydroxide (50%) | 1-10 | 1-10 | 1-10 | 1-10 |
| RU Silicate (50%) | 10-20 | 10-20 | 10-20 | 10-20 |
| Acumer 1000 (48%) | 0.1-5 | 0.1-5 | 0 | 0 |
| Acusol 425N (50%) | 0 | 0 | 2-8 | 0 |
| Belclene 810 | 0 | 0 | 0 | 2-8 |
| Sucrose | 0 | 0 | 2-8 | 2-8 |
| Average Film Score | 1 | 2 | 2.75 | 2 |
| Average Light Box Score | 14161 | 24871 | 44528 | 25590 |

The removal of the builder (EXP2) showed a decrease in efficacy in both film and light box ratings. The replacement of both the builder and the water conditioning agent with a combination of Acusol 425N and sucrose (EXP3) demonstrated film and light box ratings that were unsuccessful at 17 grain hardness water. The replacement of both the builder and the water conditioning agent with a combination of Belclene 810 and sucrose (EXP 4) showed a decrease in efficacy in both film and light box ratings.

As demonstrated, the use of a non-caustic alkalinity (e.g silicate) requires the inclusion of the builder according to the invention. As shown in EXP3 and EXP4 not all builders were efficacious according to the invention. EXP3 shows a light box score of greater than 44,000 which results in a very white glass, with hard water scaling on the surface that is very visible. In addition, EXP2 and EXP4 resulted in visible hard water scaling.

As can be seen in Table 3, the compositions of the invention provide caustic-free alkalinity detergent compositions. The caustic-free compositions were most effective at removing scale when the Trilon M chelating and threshold agent is combined with both a builder and a water conditioning agent, demonstrating synergistic efficacy according to the invention.

Example 4

An additional experimental formula providing a low alkaline detergent composition was evaluated. The experimental composition is shown in Table 4. The Control set forth in Example 1 was employed.

TABLE 4

| Description | EXP5 |
| --- | --- |
| Softened Water | 50-90 |
| Trilon M (40%) | 1-5 |
| Bayhibit AM (50%) | 1-5 |
| Sodium Hydroxide (50%) | 0 |
| RU Silicate (50%) | 10-20 |
| Acumer 1000 (48%) | 0.1-5 |

EXP5 formulation provides a low alkaline, liquid detergent composition having a distinction formulation that does not require or include sodium hydroxide as a raw material to react with the sodium silicate. As a result, there is effectively no formation of a metasilicate and the pH of the solution (and concentration formulation) is lower. In some embodiments the pH of the concentrate formulation is below about 11.5. Accordingly, the sodium hydroxide (or any alkali metal hydroxide) is removed from both the raw materials formulated into the composition and the resulting liquid detergent composition.

The experimental formula EXP5 was evaluated using the 100 cycle test set forth according to the methods of Example 2 to determine the impact of removal of caustic and decreased pH of the liquid low alkaline detergent compositions on the cleaning efficacy. The temperatures throughout the 100 cycles were adjusted to 122° F. as necessary.

The sum of the light box score for the EXP5 was 68,969, with a light box score for the plastic tumbler of 32,120. This gives a sum of 101,089 for the glasses and the plastic tumbler combined illustrating the cleaning efficacy of EXP5 according to embodiments of the invention in comparison to results for the Control (see Example 2). The experimental formula (EXP5) demonstrates efficacy of detergent composition having removal of caustic and decreased pH while maintaining acceptable cleaning efficacy and threshold effect with regard to scale build-up. EXP5 demonstrates the compositions of the invention providing low alkaline and lower pH alkalinity detergent compositions provide at least substantially similar cleaning performance as the comparison control.

Example 5

A 7 cycle glass cleaning experiment was conducted using a ES-2000 ware wash machine employing 1000 ppm Control formulation for a comparison point to the EXP5 according to the invention. Initially, about 12.88 grams food soil was weighed out in 10 plastic cups. For each cycle, half of the plastic cups were soiled with a Campbell's Cream of Chicken soup and whole milk mixture and placed in a 160° F. oven for 8 minutes before being placed back on the ware wash rack and ran for one cycle. Rinse temperatures were measured throughout the each cycle with a range of 110° F-130° F.

The Control was further evaluated to determine the impact of removal of caustic and decreased pH of the liquid caustic-free detergent compositions on the removal of protein residue as a component of cleaning efficacy. A methanol/acetic acid rinse for Coomassie Blue staining was prepared with deionized water (910 grams DI water, 910 grams methanol, 1.8 grams acetic acid). The glasses having completed the 7 cycle test were sprayed with the Coomassie Blue stain and rinsed with the methanol/acetic acid rinse. Thereafter the glasses and cups were graded for protein residue. The ware ratings range from (1) no protein residue to (5)

heavy protein residue. The results for the Control show an average of 1.0 for redeposition glasses and average of 4.5 for soiled glasses.

Example 6

The experimental formula EXP5 was further evaluated in combination with a sanitizing agent. EXP5 was evaluated in solution with 50 ppm sodium hypochlorite (commercially-available as XY-12, Ecolab USA Inc.) using 5 grain water. A 7 cycle cleaning test was performed using an ES-2000 ware wash machine employing 1000 ppm EXP5 in solution with 50 ppm sodium hypochlorite with 5 grain water source set forth according to the methods of Example 5. EXP5 with 50 ppm sodium hypochlorite was further evaluated to determine the impact of removal of caustic and decreased pH of the liquid low alkaline detergent compositions on the removal of protein residue as a component of cleaning efficacy. The glasses and cups were further stained with the Coomassie Blue dye and rinsed with methanol/acetic acid. Thereafter the glasses and cups were graded for protein residue. The results using EXP5 with sodium hypochlorite show an average of 1.0 for redeposition glasses and average of 1.0 for soiled glasses.

Experimental formula EXP5 providing the low alkaline detergent composition was further evaluated in combination in solution with 50 ppm sodium hypochlorite (XY-12) and 1.5 mL Ultra Dry per cycle using 5 grain water. A 7 cycle cleaning test was performed using an ES-2000 ware wash machine employing 1000 ppm EXP5 in solution with 50 ppm sodium hypochlorite and 1.5 mL Ultra Dry with 5 grain water source set forth according to the methods of Example 5. The glasses and cups were further stained with the Coomassie Blue dye and rinsed with methanol/acetic acid. Thereafter the glasses and cups were graded for protein residue. The testing was conducted to demonstrate whether the EXP5 or a rinse aid is responsible for protein removal. The results using EXP5 with sodium hypochlorite show an average of 1.0 for redeposition glasses and average of 1.0 for soiled glasses. The results using EXP5 with sodium hypochlorite and the rinse aid Ultra Dry show an average of 1.0 for redeposition glasses and average of 1.0 for soiled glasses. These results show that EXP5 according to the invention, and not the rinse aid, beneficially provide the protein removal.

According to an aspect of the invention the lower pH formulations according to the invention in combination with a sodium hypochlorite sanitizer and/or rinse aid provide improved cleaning efficacy without the inclusion of sodium hydroxide in the formulations. In a preferred aspect, there is benefit to providing the sanitizer for protein removal.

Example 7

Additional experimentation of the methods of Example 5 were conducted using the Control with 50 ppm sodium hypochlorite (XY-12) and 1.5 mL Ultra Dry per cycle using 5 grain water. The 7 cycle cleaning test was run with the temperatures measured throughout the each cycle with a range of 110° F.-130° F. The glasses and cups were further stained with the Coomassie Blue dye and rinsed with methanol/acetic acid and graded for protein residue showing an average of 1.0 for redeposition glasses and average of 1.0 for soiled glasses.

Example 8

The experimental formula EXP5 alone was run (without chlorine or rinse aid) in a 7 cycle test according to the same methods set forth above. The temperatures were measured throughout the each cycle. The glasses and cups were then stained with the Coomassie Blue dye and rinsed with methanol/acetic acid and graded for protein residue showing an average of 1.75 for redeposition glasses and average of 5.0 for soiled glasses. These results demonstrate the removal of the sanitizer (chlorine bleach) reduced the cleaning effect of EXP5 in an aspect of the invention.

The inventions being thus described, it will be obvious that the same may be varied in many ways. Such variations are not to be regarded as a departure from the spirit and scope of the inventions and all such modifications are intended to be included within the scope of the following claims. The above specification provides a description of the manufacture and use of the disclosed compositions and methods. Since many embodiments can be made without departing from the spirit and scope of the invention, the invention resides in the claims.

What is claimed is:

1. A method of cleaning using a caustic-free ware wash detergent comprising:
   providing a low alkaline detergent use composition, wherein the composition comprises from about 1 ppm to about 250 ppm aminocarboxylate, from about 1 ppm to about 250 ppm water conditioning polymer, from about 1 ppm to about 250 ppm builder, from about 5 ppm to about 1,000 ppm non-caustic alkalinity source, and water, wherein the composition is free of surfactants and reduces or eliminates scale build-up and enhances protein removal on said surfaces;
   washing a surface or article with the detergent use composition having a pH between about 8 and about 9.5;
   employing a sanitizer with the detergent use composition or a sanitizer is formulated in the low alkaline detergent use composition;
   employing a rinse aid;
   wherein the detergent use composition in the washing step is not heated above about 140° F., and
   wherein the detergent use composition contains sufficient use levels of the aminocarboxylate, water conditioning agent and builder to prevent the formation of precipitates in hard water sources.

2. The method of claim 1, wherein the method further comprises rinsing said surface with an initial rinse solution prior to washing with said detergent use composition.

3. The method of claim 1, wherein the aminocarboxylate is methylglycinediacetic acid or a sodium salt of the methylglycinediacetic acid.

4. The method of claim 1, wherein the water conditioning polymer is a polycarboxylic acid, and wherein the builder is a 2-phosphonobutane-1,2,4-tricarboxylic acid.

5. The method of claim 1, further comprising rinsing said surface with a rinse solution.

6. The method of claim 1, further comprising first diluting a concentrated low alkaline detergent composition comprising about 0.1-15 wt-% of an aminocarboxylate,
   about 0.1-15 wt-% of a water conditioning polymer, about 0.1-15 wt-% of a builder,
   about 10-60 wt-% of a non-caustic alkalinity source, and about 20-80 wt-% of water to form said use composition, wherein the concentrated detergent composition is diluted at a dilution ratio of between about 1:10 to about 1:10,000.

7. The method of claim 1, wherein the water conditioning polymer is a polyacrylate, polycarboxylate, polycarboxylic acid, or combination thereof.

8. The method of claim 1, wherein the builder is a condensed phosphate, phosphonate, organic phosphonate, or combination thereof.

9. The method of claim 1, wherein the non-caustic alkalinity source is a silicate.

10. The method of claim 1, wherein the ratio of the aminocarboxylate to the water conditioning polymer to the builder is in a ratio of from about 1:1:1 to about 5:1:10.

11. The method of claim 6, wherein the concentrated detergent comprises between about 1 wt-% and about 10 wt-% aminocarboxylate, between about 0.1 wt-% and about 10 wt-% water conditioning polymer, between about 0.1 wt-% and about 10 wt-% builder, and between about 30 wt-% and about 80 wt-% water.

12. The method of claim 6, wherein the concentrated detergent has a ratio of the methylglycinediacetic acid to the water conditioning polymer to the builder is from about 1:1:1 to about 5:1:10.

13. The method of claim 6, wherein the concentrated detergent comprises between about 1 wt-% and about 10 wt-% methylglycinediacetic acid, between about 1 wt-% and about 10 wt-% water conditioning polymer, between about 1 wt-% and about 8 wt-% builder, between about 10 wt-% and about 50 wt-% alkalinity source, and between about 30 wt-% and about 60 wt-% water.

14. The method of claim 1, wherein the ratio of the aminocarboxylate to the water conditioning polymer is from about 1:3 to about 3:1.

15. The method of claim 1, wherein the ratio of the aminocarboxylate to the builder is from about 1:5 to about 5:1.

16. The method of claim 1, wherein the ratio of the water conditioning agent to the builder is from about 1:5 to about 5:1.

17. The method of claim 1, wherein the ratio of the aminocarboxylate to the alkalinity source is from about 1:5 to about 1:100.

18. The method of claim 1, wherein the aminocarboxylate comprises methylglycinediacetic acid (MGDA), glutamic acid-N,N-diacetic acid (GLDA), diethylenetriaminepentaacetic acid (DTPA), diethylenetriaminepentaacetic acid, N-hydrox.yethyl ethylenediaminetriacetic acid (HEDTA), ethylenediaminetetraacetic acid (EDTA), or combinations thereof.

19. The method of claim 1, wherein the sanitizer is sodium hypochlorite.

* * * * *

UNITED STATES PATENT AND TRADEMARK OFFICE
CERTIFICATE OF CORRECTION

PATENT NO. : 10,011,809 B2
APPLICATION NO. : 15/433157
DATED : July 3, 2018
INVENTOR(S) : Dalquist et al.

Page 1 of 1

It is certified that error appears in the above-identified patent and that said Letters Patent is hereby corrected as shown below:

In Column 28, Line 19, Claim 18:
DELETE "N-hydrox.yethyl" and
INSERT --N-(hydroxyethyl)--

In Column 28, Line 23, Claim 19:
DELETE "hypochlorite"
INSERT --hypochloride--

Signed and Sealed this
Eighteenth Day of September, 2018

Andrei Iancu
*Director of the United States Patent and Trademark Office*